US008445657B2

(12) United States Patent
Shewale et al.

(10) Patent No.: US 8,445,657 B2
(45) Date of Patent: May 21, 2013

(54) MULTIPLEX COMPOSITIONS AND METHODS FOR QUANTIFICATION OF HUMAN NUCLEAR DNA AND HUMAN MALE DNA AND DETECTION OF PCR INHIBITORS

(75) Inventors: Jaiprakash Shewale, Santa Clara, CA (US); Manohar Furtado, San Ramon, CA (US); Pius Brzoska, Woodside, CA (US); Maura Barbisin, San Mateo, CA (US); Rixun Fang, Menlo Park, CA (US); Michael Malicdem, Santa Clara, CA (US); Cristin O'Shea, Mountain View, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 13/219,400

(22) Filed: Aug. 26, 2011

(65) Prior Publication Data

US 2012/0015370 A1 Jan. 19, 2012

Related U.S. Application Data

(62) Division of application No. 12/034,634, filed on Feb. 20, 2008, now Pat. No. 8,012,691.

(60) Provisional application No. 60/890,817, filed on Feb. 20, 2007.

(51) Int. Cl.
*C07H 21/04* (2006.01)
(52) U.S. Cl.
USPC ........................................ 536/23.1; 536/24.3
(58) Field of Classification Search
None
See application file for complete search history.

(56) References Cited

U.S. PATENT DOCUMENTS

| | | | |
|---|---|---|---|
| 5,952,202 A | 9/1999 | Aoyagi et al. | |
| 8,012,691 B2 | 9/2011 | Shewale et al. | |
| 2003/0077622 A1* | 4/2003 | WalkerPeach et al. | 435/6 |
| 2005/0064489 A1 | 3/2005 | Zhang et al. | |
| 2006/0252081 A1 | 11/2006 | Hyldig-Neilsen et al. | |

OTHER PUBLICATIONS

"International Application No. PCT/US08/54477", International Preliminary Report mailed Aug. 26, 2009.
"International Application No. PCT/US08/54477", Written Opinion mailed on Sep. 23, 2008.
Alonso, "Real-time PCR designs to estimate nuclear and mitochondrial DNA copy number in forensic and ancient DNA studies.", *Forensic Science Internal*, 139 2004, 141-149.
Barbisin, "Development Validation of the Qualifier Duo DNA Quantification Kit for Simultaneous Quantification of Total Human and Human Male DNA and Detection of PCR Inhibitors in Biological Samples", *Journal of Forensic Sciences* vol. 54, No. 2, Mar. 2009, 305-319.
Buck, "Design strategies and performance of custom sequencing primers", *BioTechniques*, 27 1999, 528-536.
Authorized Officer, David C. Thomas, "International Search Report", *International Searching Authority*, 4 pages (2008).
Green, "Development and validation of the Quantifiler® Real-time PCR kits for the quantification of human nuclear DNA samples", *Journal of Forensic Sciences* vol. 50, Issue 4, Jul. 2005, 809-825.
Hudlow, "A quadruplex real-time qPCR assay for the simultaneous assessment of total human DNA, human male DNA, DNA degradation and the presence of PCR inhibitors in forensic samples: A diagnosis tool for STR typing", *Forensic Science International: Genetics* vol. 2, 2008, 108-125.
Krenke, "Developmental Validation of a Real-Time PCR Assay for the Quantitation of Total Human and Male DNA", *Abstract, 18th International Symposium on Human Identification*, Hollywood, California, Promega Corporation, 2800 Woods Hollow Road, Madison, WI 53711, 2007.
Krenke, "Validation of a real-time PCR assay for the simultaneous quantification of total human and male DNA", *Plexor HY System* 18th International Symposium on Human Identification, Hollywood, California, Oct. 1-4, 2007.
Shewale, "A multiplexed system for quantification of total human and human male DNA", *Proc. AAFS 59th Annual Scientific Meeting*, San Antonio, Texas, Abstract #B100 Feb. 19-24, 2007.
Shewale, "A multiplexed system for quantification of Y-DNA and total human DNA", *Proc. 17th International Symposium on Human Identification*, Nashville, TN, USA Oct. 9-12, 2006.
Su, "Identification of the Transcriptional Unit, Structural Organization, and Promoter Sequence of the Human Sex-determining Region Y (SRY) Gene, Using a Reverse Genetic Approach", vol. 52 1993, 24-38.
Swango, "A quantitative PCR assay for the assessment of DNA degradation in forensic samples", *Forensic Science International* vol. 158, Issue 1, Apr. 20, 2006, 14-26.
Swango, "Developmental validation of a multiplex qPCR assay for assessing the quantity and quality of nuclear DNA in forensic samples", *Forensic Science International* vol. 170, No. 1, Oct. 27, 2006, 35-45.
Walker, "Multiplex polymerase chain reaction for simultaneous quantitation of human nuclear, mitochondrial, and male Y-chromosome DNA: application in human identification", *Analytical Biochemistry* vol. 337, 2006, 89-97.

* cited by examiner

*Primary Examiner* — Kenneth R. Horlick
*Assistant Examiner* — David Thomas (57) ABSTRACT

The invention relates to a method for simultaneous quantification of human nuclear DNA and human male DNA in a biological sample while also detecting the presence of PCR inhibitors in a single reaction. The multiplex quantification method also provides a ratio of human nuclear and male DNA present in a biological sample. Such sample characterization is useful for achieving efficient and accurate results in downstream molecular techniques such as genotyping.

8 Claims, 7 Drawing Sheets

New Plasmid Construct with 130 bp IPC Template Insert

CATCCGCACACTATCTCATCGTTTGTAGGGTTACGGGCCAGAT
GACTCCATTCTTATCCCCTGAAAACATTCTATTTGTACGCCATA
GTGGCCTCGTTGATCTTCCGTTGATAGTGTGGCGGTTGGA

FIG. 7

SEQUENCE LISTING

```
<160> NUMBER OF SEQ ID NOS: 13

<210> SEQ ID NO 1
<211> LENGTH: 130
<212> TYPE: DNA
<213> ORGANISM: Artificial Sequence
<220> FEATURE:
<223> OTHER INFORMATION: synthetic sequence

<400> SEQUENCE: 1
catccgcaca ctatctcatc gttttgtagg gttacgcggc cagatgactc catcttatcc      60
ccttgaaaac attcttattt gtacgccata gtggcctcgt tgatcttccg ttgatagtgt     120
ggcggttgga                                                             130

<210> SEQ ID NO 2
<211> LENGTH: 79
<212> TYPE: DNA
<213> ORGANISM: Artificial Sequence
<220> FEATURE:
<223> OTHER INFORMATION: synthetic sequence

<400> SEQUENCE: 2
catccgcaca ctatctcatc gttatcgttc catcagctcg ttgatcttcc gttctggcat      60
tgatagtgtg gcggttgga                                                   79

<210> SEQ ID NO 3
<211> LENGTH: 140
<212> TYPE: DNA
<213> ORGANISM: Homo sapiens

<400> SEQUENCE: 3
acagactcac ggccagcgaa gtgagttcaa tggctgaggt gaggtacccc gcagggacc       60 tcataaccca attcagacta ctctcctccg cccatttttg gaaaaaaaaa aaaaaaaaa      120 aaacaaaacg aaaccgggcc                                                 140

<210> SEQ ID NO 4
<211> LENGTH: 130
<212> TYPE: DNA
<213> ORGANISM: Homo sapiens

<400> SEQUENCE: 4 gcttttttgtg tcctctcgtt ttgtgacata aaggtcaat gaaaaaattg gcgattaagt      60
caaattcgca tttttcagga cagcagtaga gcagtcaggg aggcagatca gcagggcaag    120
tagtcaacgt                                                            130
```

```
<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
acagactcac ggccagcgaa                                                  20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ggcccggttt cgttttgttt t                                                21

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7 gcttttgtg tcctctcgtt ttgtgaca                                          28

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
acgttgacta cttgccctgc tgat                                             24

<210> SEQ ID NO 9
<211> LENGTH: 16
<212> TYPE: DNA
<213> ORGANISM: Artificial Sequence
<220> FEATURE:
<223> OTHER INFORMATION: probe

<400> SEQUENCE: 9
cagccattga actcac                                                      16

<210> SEQ ID NO 10
<211> LENGTH: 20
<212> TYPE: DNA
<213> ORGANISM: Artificial Sequence
<220> FEATURE:
<223> OTHER INFORMATION: probe

<400> SEQUENCE: 10
ttttcaggac agcagtagag                                                  20

<210> SEQ ID NO 11
<211> LENGTH: 22
<212> TYPE: DNA
<213> ORGANISM: Artificial Sequence
<220> FEATURE:
<223> OTHER INFORMATION: primer
```

```
<400> SEQUENCE: 11
catccgcaca ctatctcatc gt                                              22

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tccaaccgcc acactatcaa                                                 20

<210> SEQ ID NO 13
<211> LENGTH: 15
<212> TYPE: DNA
<213> ORGANISM: Artificial Sequence
<220> FEATURE:
<223> OTHER INFORMATION: probe

<400> SEQUENCE: 13
ctcgttgatc ttccg                                                      15
```

MULTIPLEX COMPOSITIONS AND METHODS FOR QUANTIFICATION OF HUMAN NUCLEAR DNA AND HUMAN MALE DNA AND DETECTION OF PCR INHIBITORS

CROSS REFERENCE TO RELATED APPLICATIONS

This application is a Divisional of U.S. patent application Ser. No. 12/034,634, filed Feb. 20, 2008, now U.S. Pat. No. 8,012,691, issuing on Sep. 6, 2011 and claims a priority benefit under 35 U.S.C. §119(e) to U.S. Provisional Application No. 60/890,817, filed Feb. 20, 2007, the contents of which are incorporated herein by reference.

FIELD OF THE INVENTION

The invention relates to methods and compositions for quantification of DNA and detection of PCR inhibitors in a biological sample.

INTRODUCTION

DNA Typing

DNA (Deoxyribonucleic acid) typing is commonly used to identify the parentage of human children, and to identify the source of blood, saliva, semen, and other tissue found at a crime scene or other sites requiring identification of human remains. DNA typing involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e. "locus") of DNA in which such a variation occurs is referred to as a "polymorphic locus."

Genetic markers which are sufficiently polymorphic with respect to length or sequence have long been sought for use in identity applications, such as paternity testing and identification of biological samples collected for forensic analysis. The discovery and development of such markers and methods for analyzing such markers have gone through several phases of development over the last several years.

By the early 1990s, the use of polymerase chain reaction (PCR) technology (disclosed in U.S. Pat. No. 4,683,202 (1987)) was combined with the analysis of loci. (See, K. Kasai et al., Amplification of a Variable Number of Tandem Repeats (VNTR) Locus (pMCT118) by the Polymerase Chain Reaction (PCR) and its Application to Forensic Science, *J. Forensic Sci.* 35(5):1196 1200 (1990)). The amplified products are separated through agarose or polyacrylamide gels and detected by incorporation of radioactivity during the amplification or by post-staining with silver or ethidium bromide. However, PCR can only be used to amplify relatively small DNA segments reliably, i.e. only reliably amplifying DNA segments under 3,000 bases in length. (See, M. Ponce et al., PCR amplification of long DNA fragments, *Nucleic Acids Res.* 20(3):623 (1992); R. Decorte et al., Rapid Detection of Hypervariable Regions by the Polymerase Chain Reaction Technique, *DNA And Cell Biol.* 9(6):461 469 (1990)).

In recent years, the discovery and development of polymorphic short tandem repeats (STRs) as genetic markers has played an important role in DNA typing. In this approach, amplified alleles at each selected locus may be differentiated based on length variation. Amplification protocols with STR loci can be designed to produce small products, generally from 60 to 500 base pairs (bp) in length, and alleles from each locus are often contained within a range of less than 100 bp. This allows simultaneous electrophoretic analysis of several STR loci (or markers) on the same gel or capillary electrophoresis by careful design of PCR primers such that all potential amplification products from an individual system do not overlap the range of alleles of other systems.

Gender Assays

Determination of gender from human DNA samples is a common problem in forensics laboratories and in prenatal gender determination. While several assays based on use of the polymerase chain reaction (PCR) are currently available for human sex typing, each of the current approaches has limitations.

Certain methods are based on male-specific amplification, such as the amplification of the SRY locus (SRY). (See, A. H. Sinclair, et al., A Gene from the Human Sex-Determining Region Encodes a Protein with Homology to a Conserved DNA-Binding Motif, *Nature* 346:240 244 (1990)). These methods, however, lack an internal positive control to discriminate between female DNA and male DNA which has failed to amplify for technical reasons.

Restriction fragment length polymorphism (RFLP) assays can be based on sex-specific mutations at the ZFX/ZFY. See R. Reynolds, et al., Gender Determination of Forensic Samples Using PCR Amplification of ZFX/ZFY Gene Sequences, *J. Forensic Sci.* 41:279 286 (1996). RFLP assays, however, require a second enzyme digestion or hybridization step following the initial PCR amplification.

Another method proposed by Cali, et al., *Int. J. Legal Med.* 116:133 138 (2002), is based on a single adenine insertion within a tandem repeat array at the DXYS156 locus. But this assay requires access to allele detection equipment potentially unavailable to forensics labs with limited resources.

A very widely used approach is based on the Amelogenin locus, which yields different sized PCR amplicons for the X and Y chromosome versions of the Amelogenin gene. (See, K. M. Sullivan, et al., A rapid and quantitative DNA sex test: fluorescence-based PCR analysis of X-Y homologous gene amelogenin, *Biotechniques* 15:636 638, 640 631 (1993). However, this method misidentifies males as females in some cases (a frequency of 0.018% in Caucasian males, 1.85% among Indians, and as high as 8% in Sri-Lankans) due to a deletion in the AMEL Y region. (See, F. R. Santos, et al., Reliability of DNA-Based Sex Tests, *Nat. Genet.* 18:103 (1998); M. Steinlechner, et al., Rare Failures in the Amelogenin Sex Test, *Int. J. Legal Med.* 116:117 120 (2002); K. Thangaraj, et al., Is the Amelogenin Gene Reliable for Gender Identification in Forensic Casework and Prenatal Diagnosis?, *Int. J. Legal Med.* 116: 121 123 (2002)). While the frequency of the deletion is relatively low, the crucial nature of forensic test results in circumstances such as rape and prenatal gender determination where there is risk for male-specific inherited disorders, makes any source of error a legitimate cause for concern. This has led several researchers to recommend that Amelogenin not be relied upon as the sole determinant of gender. (See, Santos, supra; Steinlechner, supra; Thangaraj, supra; B. Brinkmann, Is the Amelogenin Sex Test Valid?, *Int. J. Legal Med.* 116:63 (2002).)

Alu Elements

Alu elements are transposable genetic elements which have amplified throughout primate evolution and now comprise roughly 10% of the human genome. Alu insertions are generally considered to be homoplasy-free with respect to human population genetics, as the probability of two Alu elements independently inserting in the same genomic location is extremely small. (See, M. A. Batzer, et al., Alu Repeats and Human Genomic Diversity, *Nat. Rev. Genet.* 3:370 379 (2002)).

In the field of forensic DNA analysis, these methods are often used to characterize evidence by comparing the STR profile, either autosomal or Y-chromosomal, of evidence sample with the profiles for reference samples obtained from a victim and a suspect. Contribution of the suspect to the evidence sample is determined by the interpretation of STR profiles. Many genotyping multiplex kits such as Profiler Plus®, COfiler®, Identifiler® and MiniFiler™ (Applied Biosystems, Foster City, Calif.) have been developed for genotyping. In general, the genotyping protocol involves extraction of DNA from the biological sample, quantification of the DNA, amplification for STR loci and fragment analysis on a Genetic Analyzer. Quantification of human nuclear DNA in a biological sample is an important step during STR profiling of a sample, especially for a forensic sample. This is because it is important to obtain an interpretable STR profile from forensic evidence sample which very often contains non human DNA and other contaminants.

Hybridization-based quantification methods e.g., Quantiblot® membrane that are traditionally used for the quantification of DNA in forensic samples are generally considered time-consuming, labor-intensive and not suitable for automation. Further, it is difficult to predict the amplitude of the STR profile because of the difference in the sensitivity of quantification methods and STR genotyping systems.

Real-time PCR assays like Quantifiler® Human DNA Quantification Kit and Quantifiler® Y Human Male DNA Quantification Kit (Applied Biosystems, Foster City, Calif.), as well as AluQuant® (Promega, Wis.), are useful tools for this type of analysis. However, in order to obtain the quantity of human nuclear and human male DNA in a sample using commercially available Quantifiler® kits, it is necessary to run two separate quantification assays. This approach consumes more quantity of forensic sample, which is often present in limited quantities, as well as time and reagents.

Newer multiplex TaqMan® real-time assays described by Walker et al., *Anal. Biochem.* 337 (2005) 89-97; Horsman et al., *J. Forensic Sci.* 51 (2006) 758-765; and Nicklas and Buel *Forensic Sci. Intl. In Press*, while simultaneously obtaining mixture ratios of human male and female DNA have the disadvantage of failing to detect inhibitors of PCR in the same reaction sample.

An assay described by Swango et al., *Forensic Sci Int.* 2006 Oct. 27; [Epub ahead of print], provides for obtaining a mixture ratio as well as detection of the inhibitors of PCR. However, the human nuclear DNA amplification target THO1 (human tyrosine hydroxylase gene on chromosome 11) spans the polymorphic STR region. THO1 is a commonly used locus for human identification in forensic laboratories. (See, e.g. J. M. Butler, Forensic DNA Typing. $2^{nd}$ ed. Elsevier Academic Press, Burlington, 2005). Incorporation of such a polymorphic STR target in the quantification assay is generally discouraged in forensic laboratories to avoid possible contamination incidences. Avoiding such contamination is critical in analyzing mixed forensic evidence samples (See e.g. T. R. Moretti, A. L. Baumstark, D. A. Defenbaugh, K. M. Keys, J. B. Smerick, B. Budowle, Validation of short tandem repeats (STRs) for forensic usage: performance testing of fluoroscent multiplex STR systems and analysis of authentic and simulated forensic samples, J. Forensic Sci. 46 (2001) 647-660). Secondly, the length of THO1 amplicon will vary by 44 nucleotides since alleles ranging from 3 to 14 repeat units have been characterized in different human population groups (See e.g., Brinkmann, B., Sajantila, A., Goedde, H. W., Matsumoto, H., Nishi, K. and Wiegand, P. (1996) Population genetic comparisons among eight populations using allele frequency and sequence data from three microsatellite loci. Eur. J. Hum. Genet. 4: 175-182; van Oorschot, R. A. H., Gutowski, S. J. and Robinson, S. L. (1994) HUMTH01: Amplification, species specificity, population genetics and forensic applications. Int. J. Leg. Med. 107: 121-126; Espinheira, R., Geada, H., Ribeiro, T. and Reys, L. (1996) STR analysis—HUMTH01 and HUMFES/FPS for forensic application. Advances in Forensic Haemogenetics. Volume 6, p. 528; Gene, M., Huguet, E., Moreno, P., Sanchez, C., Carracedo, A. and Corbella, J. (1996) Population study of the STRs HUMTH01 (including a new variant) and HUMVWA31A in Catalonia (northeast Spain). Int. J. Legal Med. 108: 318-320; Klintschar, M., Kozma, Z., Al Hammadi, N., Fatah, M. A., and Nohammer, C. (1998), A study on the short tandem repeat systems HumCD4, HumTH01, and HumFIBRA in population samples from Yemen and Egypt. Int. J. Legal Med. 111(2):107-109; Griffiths, R. A. L., Barber, M. D., Johnson, P. E., Gillbard, S. M., Haywood, M. D., Smith, C. D., Arnold, J., Burke, T., Urquhart, A., and Gill, P. (1998), New reference allelic ladders to improve allelic designation in a multiplex STR system. Int. J. Legal Med. 111 (5):267-272). Although the detection probe is designed outside the polymorphic region, the possibility of variation in the efficiency of this assay due to the variation in the length of amplicon cannot be ruled out.

The utility of such assays lie in their specificity for detecting a desired loci. Heretofore, it has not been possible to simultaneously quantitate human nuclear DNA and human male DNA (which rely upon specific amplification of a desired loci) and also to simultaneously ascertain the accuracy of said quantitating, by detecting the presence of PCR inhibitors in one reaction. The difficulty in detecting PCR inhibitors in such a reaction is to identify a target DNA segment for amplification that is both sensitive to inhibitors and does not interfere with or bind to the human loci amplicon or loci specific primers. Thus, there is a need for a simple, reliable, and sensitive assay system for simultaneously quantitating human nuclear DNA and human male DNA, and for detecting the presence of PCR inhibitors in a sample, in one reaction.

SUMMARY OF THE INVENTION

Various embodiments of the present teachings comprise simultaneous methods for quantitating human nuclear DNA and male DNA, and detecting the presence of PCR inhibitors in a biological sample. Embodiments of the invention comprise multiplex TaqMan® Real-Time PCR assays.

In other embodiments, the present teachings relate to novel IPC targets SEQ ID NO: 1 and SEQ ID NO: 2. In yet additional embodiments, the methods encompass a plasmid comprising the novel IPC target of SEQ ID NO: 1 or SEQ ID NO: 2.

In further embodiments, kits are provided for multiplex Real-Time PCR assays (including for use in TaqMan® based assays, (Applied Biosystems Foster City, Calif.)) for quantitating human nuclear DNA and male DNA, and simultaneously ascertaining the accuracy of said quantitation by detecting the presence of PCR inhibitors in a biological sample.

Methods of the present teachings relate to a method for quantitating human nuclear DNA and human male DNA in a sample and simultaneously ascertaining the accuracy of said quantitation, the method comprising:

combining the sample under amplification conditions with
primer pairs capable of specifically amplifying a 60-500
base pair sequence comprising human specific RPPH1,
and a 60-500 base pair sequence comprising human
male specific SRY loci;
an internal plasmid control (IPC) comprising SEQ ID
NO:1, and a primer pair capable of amplifying a 60-500
base pair sequence comprising SEQ ID NO:1;
labeled probes for detecting the amplified RPPH1, SRY,
and SEQ ID NO:1;
waiting for amplification of the loci or plasmid sequence by
a multiplex real-time polymerase chain reaction (PCR); and
determining the amount of the amplified loci and plasmid
sequence, wherein the amount of amplified loci provides a
quantitative value of the amount of the amplified loci and the
amount of the amplified plasmid sequence indicates the accuracy of said quantitation.

In certain embodiments, the method encompasses an internal plasmid control (IPC) comprising SEQ ID NO:2, and a primer pair capable of amplifying a 60-500 base pair sequence comprising SEQ ID NO:2; and a labeled probe for detecting the amplified SEQ ID NO:2.

In certain embodiments, the human RPPH1 locus has the sequence SEQ ID NO:3.

In certain embodiments, the primers capable of amplifying human RPPH1 locus have the sequence SEQ ID NO:5 and SEQ ID NO:6, respectively.

In certain embodiments, the human SRY locus has the sequence SEQ ID NO: 4.

In certain embodiments, the primers capable of amplifying human SRY locus have the sequence SEQ ID NO:7 and SEQ ID NO:8, respectively.

In certain embodiments, the primers capable of amplifying SEQ ID NO:1 have the sequence SEQ ID NO:11 and SEQ ID NO:12, respectively.

In certain embodiments, the labeled probes are labeled with a first, second, and third fluorescent moiety that produces a detectable signal upon release of the labeled probe from being bound to its target DNA or plasmid, and the released probes are detected by real-time measurement of an amount of fluorescent emission;
wherein the amount of fluorescent emission of each released labeled probe from being bound to the amplified loci provides a quantitative value of the amount of the amplified loci, and the amount of fluorescent emission detected by the release of the labeled probe to the plasmid sequence indicates the accuracy of said quantitation, the quantity of the released labeled probe to the plasmid sequence correlating inversely with the presence of PCR inhibitors.

In certain embodiments, the labeled probes have the sequence SEQ ID NO: 9, SEQ ID NO: 10 and SEQ ID NO: 13.

In certain embodiments, the RPPH1 probe is labeled with FAM; the SRY probe is labeled with VIC, and the SEQ ID NO:1 probe is labeled with NED.

In certain embodiments, the RPPH1 probe is labeled with FAM; the SRY probe is labeled with VIC, and the SEQ ID NO:2 probe is labeled with NED.

Kits of the present teachings relate to primer pairs capable of specifically amplifying human RPPH1, and human SRY loci; and an internal plasmid control (IPC) comprising SEQ ID NO:1, and a primer pair capable of specifically amplifying SEQ ID NO:1.

In certain embodiments, kits of the present teachings also include labeled probes for detecting the amplified human RPPH1 locus, the amplified human SRY locus, and amplified SEQ ID NO:1.

In certain embodiments, kits of the present teachings include labeled probes wherein the RPPH1 probe is labeled with FAM; the SRY probe is labeled with VIC, and the SEQ ID NO:1 probe is labeled with NED.

Kits of the present teachings may also contain PCR reaction mix, a quantification standard, and a dilution buffer.

Kits of the present teachings relate to primer pairs capable of specifically amplifying human RPPH1 and human SRY loci; an internal plasmid control (IPC) comprising SEQ ID NO:2, and a primer pair capable of specifically amplifying SEQ ID NO:2.

In certain embodiments, kits of the present teachings also include a labeled probe for detecting the amplified human RPPH1 locus, the amplified human SRY locus, and SEQ ID NO:2.

In certain embodiments, kits of the present teachings include labeled probes wherein the RPPH1 probe is labeled with FAM; the SRY probe is labeled with VIC, and the SEQ ID NO:2 probe is labeled with NED.

Kits of the present teachings may also contain PCR reaction mix, a quantification standard, and a dilution buffer.

Compositions of the present teachings relate to an isolated nucleic acid having the sequence SEQ ID NO: 1, or a fragment thereof.

Compositions of the present teachings also relate to an isolated nucleic acid having the sequence SEQ ID NO: 2, or a fragment thereof.

Further compositions of the present teachings relate to a plasmid comprising the isolated nucleic acid sequence of SEQ ID NO: 1 or SEQ ID NO:2.

Yet additional compositions of the present teachings relate to an isolated host cell comprising the plasmid comprising the isolated nucleic acid sequence of SEQ ID NO: 1 or SEQ ID NO:2.

Yet additional compositions of the present teachings relate to an isolated nucleic acid having the sequence SEQ ID NO:11.

Yet additional compositions of the present teachings relate to an isolated nucleic acid having the sequence SEQ ID NO:12.

Yet additional compositions of the present teachings relate to an isolated nucleic acid having the sequence SEQ ID NO:13.

DRAWINGS

The skilled artisan will understand that the drawings, described below, are for illustration purposes only. The drawings are not intended to limit the scope of the present teachings in any way.

DESCRIPTION OF VARIOUS EMBODIMENTS OF THE INVENTION

Figure 1:
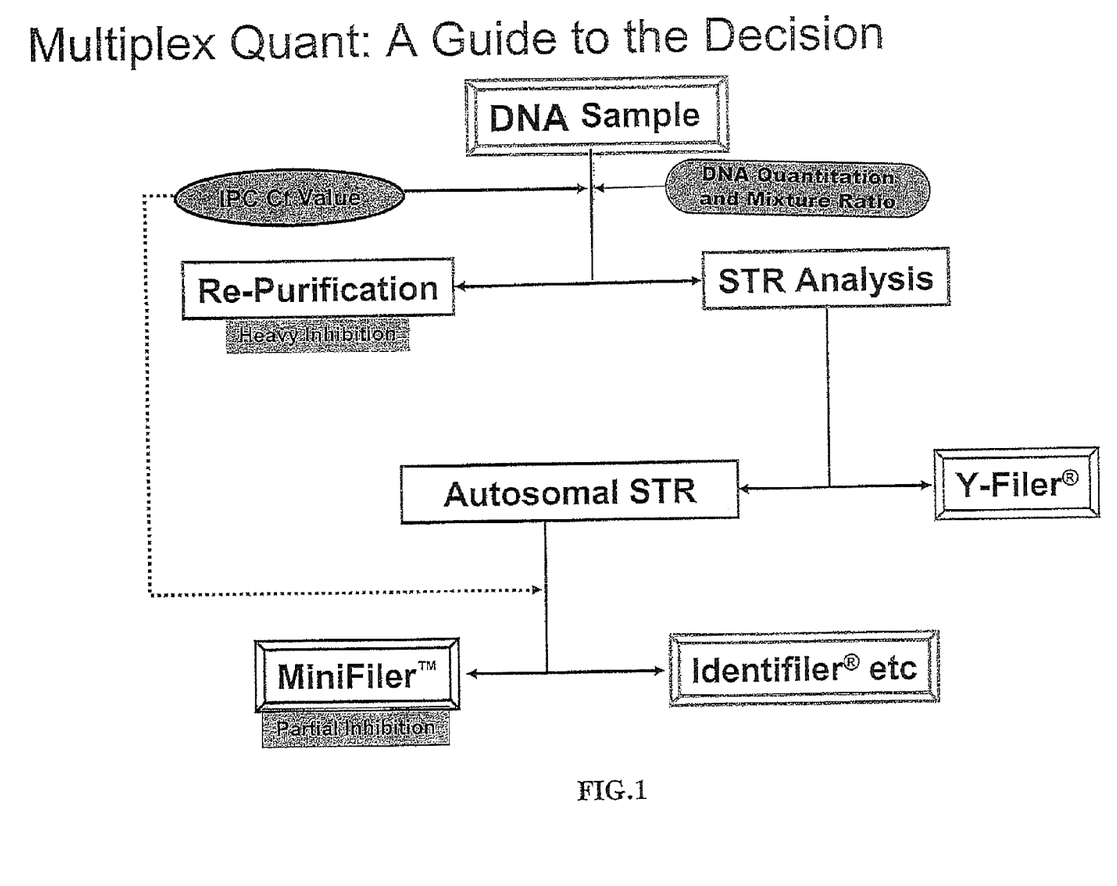
FIG. 1 is a flowchart showing various processing techniques that follow characterization of the DNA containing sample.

Human forensic work requires sensitive quantitation of human nuclear DNA (nDNA) and male Y-chromosome DNA from complex biomaterials. Simultaneous quantification of both of these constituents, while determining the presence of PCR inhibitors in a single reaction is particularly desirable. Based upon the amount of DNA present in the sample, a particular amplification system can be chosen that will yield the best results. The samples that contain a relatively small quantity of human male DNA compared to human nuclear DNA (heavy in female DNA) are preferably amplified for Y-STR loci using Yfiler® (Applied Biosystems Foster City, Calif.). Determining the presence of PCR inhibitors, facilitated by the amplification of IPC, allows for an informed choice of an STR kit that is designed for amplification of samples containing PCR inhibitors and/or degraded DNA. STR kits such as Identifiler® are designed for normal samples, while MiniFiler™ (Applied Biosystems Foster City, Calif.) is designed for amplification of samples containing PCR inhibitors and degraded DNA. When samples exhibit complete inhibition, i.e., a failure to amplify the IPC, then the extract should be repurified prior to STR analysis. Roles of the present methods in determining these downstream steps are shown in the flowchart of FIG. 1.

A typical forensic evidence sample is often a mixture of human male and female DNA. Further, the forensic biological sample is exposed to different environmental insults leading to degradation of DNA as well as contamination with the compounds that inhibit PCR. It is desirable to have the following information about the forensic evidence sample prior to amplification for STRs:

i. Quantification of human nuclear DNA for determining the quantity of extract to be used for amplification for different STR multiplex systems.

ii. Mixture ratio of human male and female DNA.

iii. Presence of PCR inhibitors.

A quantification method that measures the quantity of extract to be used for amplification is important in forensic DNA analysis. Quantification of human nuclear DNA in a biological sample is an important step for forensic DNA profiling because many forensic samples contain unknown mixtures of DNA from non human species such as parasites, fungi, bacteria, or other microorganisms, or animals. In order to obtain an interpretable STR profile, selectively amplifying human nuclear DNA is required. Information relating to the quantity of DNA as well as to the presence of inhibitors of PCR is desirable in order to optimize the STR amplification reaction.

The present methods relate to a multiplex Real-Time PCR assay for simultaneous quantification of human nuclear and human male DNA (and therefore derivation of their ratio) in a single reaction. Methods are also provided for simultaneously detecting the presence of PCR inhibitors, and thus ascertaining the accuracy of the quantification of the DNA in a biological sample.

The present methods provide optimization for quantitating desired DNA in a single reaction providing a quantitation range of 23 pg/µl to 50 ng/µl.

These and other features of the present teachings will become more apparent from the description herein.

Multiplex Assay System

The present teachings relate to a multiplexed Real Time PCR assay system, amenable to assembly in a kit, for simultaneously quantifying human nuclear DNA and human male DNA in a sample. Additionally, the system provides a novel internal PCR control (IPC) for detection of PCR inhibitors. Additionally, in certain embodiments, the teachings provide optimization of PCR assay conditions by incorporating polyhydroxy alcohols, such a glycerol into the reaction mixture in amounts ranging from 3-7% of the reaction mixture.

Standard cloning and molecular biology techniques are well known in the art and unless otherwise noted, they can be carried out according to various techniques described by Sambrook et al. (2001) Molecular Cloning: A Laboratory Manual. 3rd Ed. Cold Spring Harbor Laboratory Press: Cold Spring Harbor, N.Y., or according to various techniques described in Ausubel et al. eds. (2005) Current Protocols in Molecular Biology. John Wiley and Sons, Inc.: Hoboken, N.J.; or Ray Wu, Recombinant DNA (1980) Volume 68; Ray Wu, Lawrence Grossman, and Kivie Moldave Recombinant DNA, Part B (1983) Volume 100; or Ray Wu, Lawrence Grossman, and Kivie Moldave Recombinant DNA, Part C (1983) Volume 101.

The present multiplex assay system amplifies SRY, Ribonuclease P RNA component H1 (RPPH1, also referred to as RNase P), and an internal control for PCR inhibitors (IPC) that is a synthetic nucleotide template, all in one reaction sample. While the examples below utilize specific constructs from these loci and IPC template, other similar constructs based upon these sequences may be utilized in triplex assays based upon the presently described assays, according to particular reactions, and particular conditions. The amplified loci targets and IPC template or sequence can vary in length from 60-500 nucleotide bases depending upon the particular reaction and reaction conditions. Optimum results occur when the length of the amplified target sequences utilized together in a multiplex reaction are in close agreement, such as varying by not more than about 10 or 20 nucleotides in length.

The unique IPC template facilitates monitoring small amounts of PCR inhibitors in biological samples using real time PCR assays. The novel IPC control (SEQ ID NO: 1) comprises the following 130 nucleotide bases:

```
                                          (SEQ ID NO: 1)
5'CATCCGCACACTATCTCATCGTTTTGTAGGGTTACGCGGCCAGATGAC

TCCATCTTATCCCCTTGAAAACATTCTTATTTGTACGCCATAGTGGCCTC

GTTGATCTTCCGTTGATAGTGTGGCGGTTGGA 3'
```

A suitable forward primer for amplifying SEQ ID NO: 1 comprises: 5' CATCCGCACACTATCTCATCGT 3' (SEQ ID NO: 11). A suitable reverse primer for amplifying SEQ ID NO: 1 comprises: 5' TCCAACCGCCACACTATCAA 3' (SEQ ID NO: 12). A suitable probe for detecting SEQ ID NO: 1 comprises: 5' CTCGTTGATCTTCCG 3' (SEQ ID NO: 13). Any suitable primer for amplifying SEQ ID NO:1 or probe for detecting SEQ ID NO:1 can be used in the described methods and variations thereof according to particular reactions, and particular conditions.

In addition to the novel IPC, the amplification targets for human nuclear and human male DNA in the present assay are Ribonuclease P RNA component H1 (RPPH1, also referred to as RNase P) and SRY, respectively.

The RPPH1 target or amplicon sequence (SEQ ID NO: 3) comprises the following bases:

5'ACAGACTCACGGCCAGCGAAGTGAGTTCAATGGCTGAGGTGAGGTACC

CCGCAGGGGACCTCATAACCCAATTCAGACTACTCTCCTCCGCCCATTTT

TGGAAAAAAAAAAAAAAAAAAAAAAACAAAACGAAACCGGGCC3'

The RPPH1 target or amplicon sequence is based upon the ribonuclease P RNA component H1 from *Homo sapiens* (chromosome location 14q11.2), and is also referred to as H1 RNA and H1 RNA, with Gene ID 85495 and GenBank reference NR 002313.

The SRY target or amplicon sequence (SEQ ID NO: 4) comprises the following sequences:

5'GCTTTTTGTGTCCTCTCGTTTTGTGACATAAAAGGTCAATGAAAAAAT

TGGCGATTAAGTCAAATTCGCATTTTTCAGGACAGCAGTAGAGCAGTCAG

GGAGGCAGATCAGCAGGGCAAGTAGTCAACGT 3'

The SRY sequence is based on the *Homo sapiens* sex determining region (chromosomal location Yp11.3; GeneID 6736 and GenBank reference NM 003140), also referred to as TDF, or TDY. This region is specific, identifying human males.

The primers for amplification of RPPH1 and SRY targets are designed to generate amplicons with 140 nucleotide bases (bp) and 130 bp, respectively. The sequence of a suitable forward RPPH1 primer comprises: 5'-ACAGACTCACGGC-CAGCGAA 3' (SEQ ID NO: 5). A suitable reverse RPPH1 primer comprises: 5'-GGCCCGGTTTCGTTTTGTTTT 3' (SEQ ID NO: 6).

The sequence of a suitable forward primer for SRY comprises: 5' GCTTTTTGTGTCCTCTCGTTTTGTGACA 3' (SEQ ID NO: 7). The reverse SRY primer comprises: 5' ACGTTGACTACTTGCCCTGCTGAT 3' (SEQ ID NO: 8).

A suitable probe for detecting the presence of the RPPH1 target/amplicon comprises: 5' CAGCCATTGAACTCAC 3' (SEQ ID NO: 9).

A suitable probe for detecting the presence of the SRY target/amplicon comprises: 5' TTTTCAGGACAGCAGTA-GAG 3' (SEQ ID NO: 10).

Initially, multiplex assays were conducted using a 79 base IPC template (SEQ ID NO: 2) These initial assays produced a Ct value that did not shift in the presence of up to 15 μM hematin and 7.5 ng/μl humic acid when using a PCR Master Mix containing 40 ng/μl BSA in the final reaction indicating an insensitivity to these amplification inhibitors, at these concentrations. Reactions including the 79 base pair IPC template detected the presence of higher amounts of hematin and humic acid and are useful under certain conditions.

The 79 bp IPC template comprises the following bases sequences:

(SEQ ID NO: 2)
CATCCGCACACTATCTCATCGTTATCGTTCCATCAGCTCGTTGATCTTCC

GTTCTGGCATTGATAGTGTGGCGGTTGGA

Compared to the amplification of RPPH1 and SRY target sequences, the amplification of the SEQ ID NO: 2 IPC template provides a relatively different response to the PCR inhibitors in a sample. Without wishing to be bound by this theory, this effect is likely due to the difference in the amplicon size of the targets and the IPC. This differential efficiency of amplification could also be due to the greater complexity of the genomic DNA compared to the single stranded synthetic IPC template.

Figure 7:
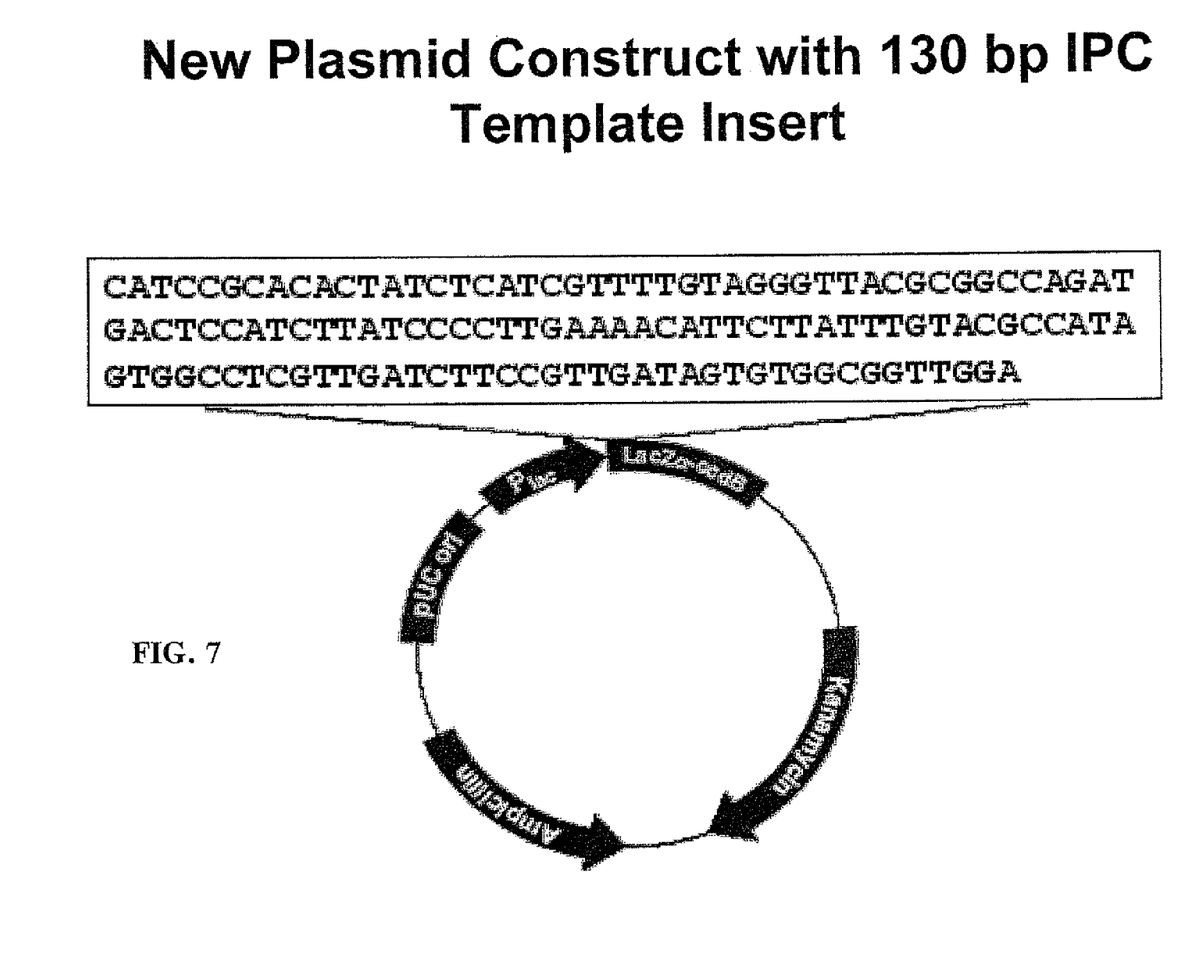
FIG. 7 is a diagram of the novel IPC plasmid containing SEQ ID NO:1.

In order to minimize effects on the target Ct due to differences in amplicon size and complexity of templates, a new 130 base IPC template (SEQ ID NO: 1) was created and cloned into a plasmid vector. The SEQ ID NO: 1, 130 bp long DNA fragment is unique and has no homology with any known human or mammalian DNA. Bacterial clones were screened for SEQ ID NO: 1. The positive clones were further used to generate a pCR®4-TOPO® (Invitrogen, Carlsbad, Calif.) plasmid containing the SEQ ID NO: 1 IPC template, according to well known techniques, and as shown in FIG. 7 (See methods described in Shuman, S. (1991). Recombination Mediated by Vaccinia Virus DNA Topoisomerase I in *Escherichia coli* is Sequence Specific. Proc. Natl. Acad. Sci. USA 88, 10104-10108; Shuman, S. (1994). Novel Approach to Molecular Cloning and Polynucleotide Synthesis Using Vaccinia DNA Topoisomerase. J. Biol. Chem. 269, 32678-32684; and Invitrogen (2006) TOPO TA Cloning® Kit for Sequencing, User Manual). The sequence of 130 base insert (SEQ ID NO: 1) in the pCR®4-TOPO® plasmid vector was verified by Sanger sequencing.

Figure 5:
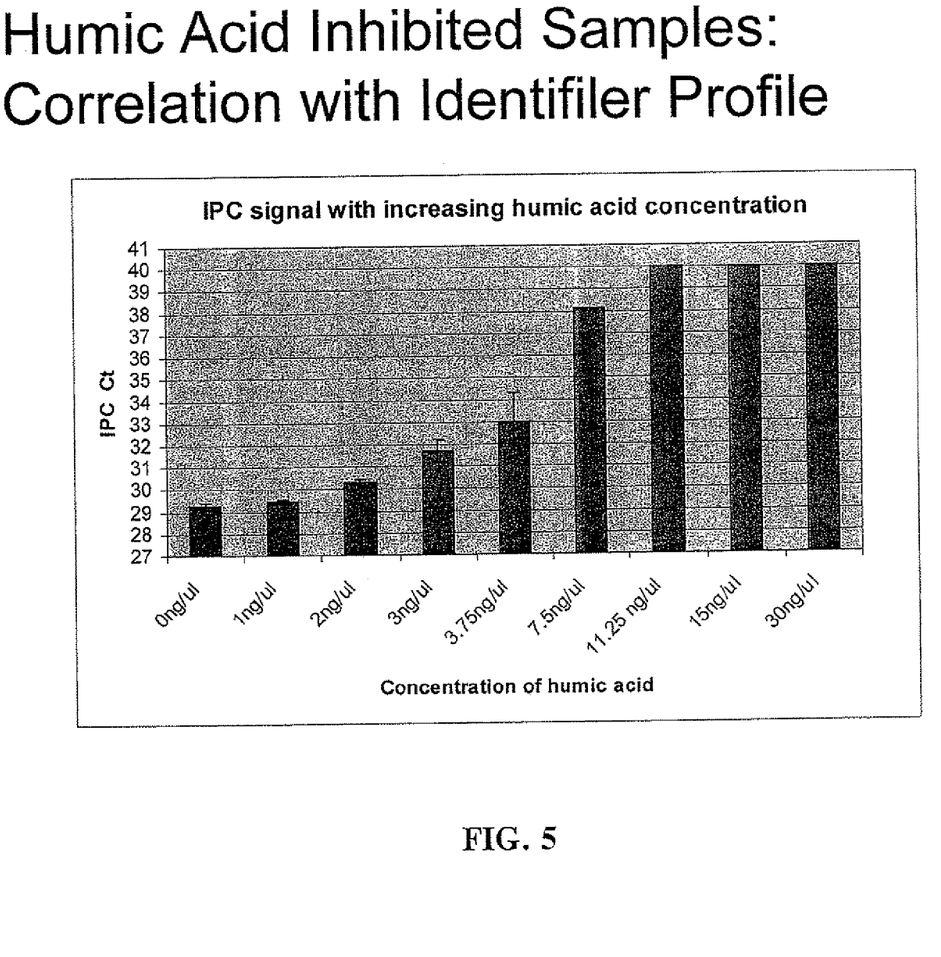
FIG. 5 is a bar graph indicating increasing IPC cycle threshold (Ct) value (decrease in IPC amplification signal) with increasing humic acid concentration for inhibited samples.
Figure 6:
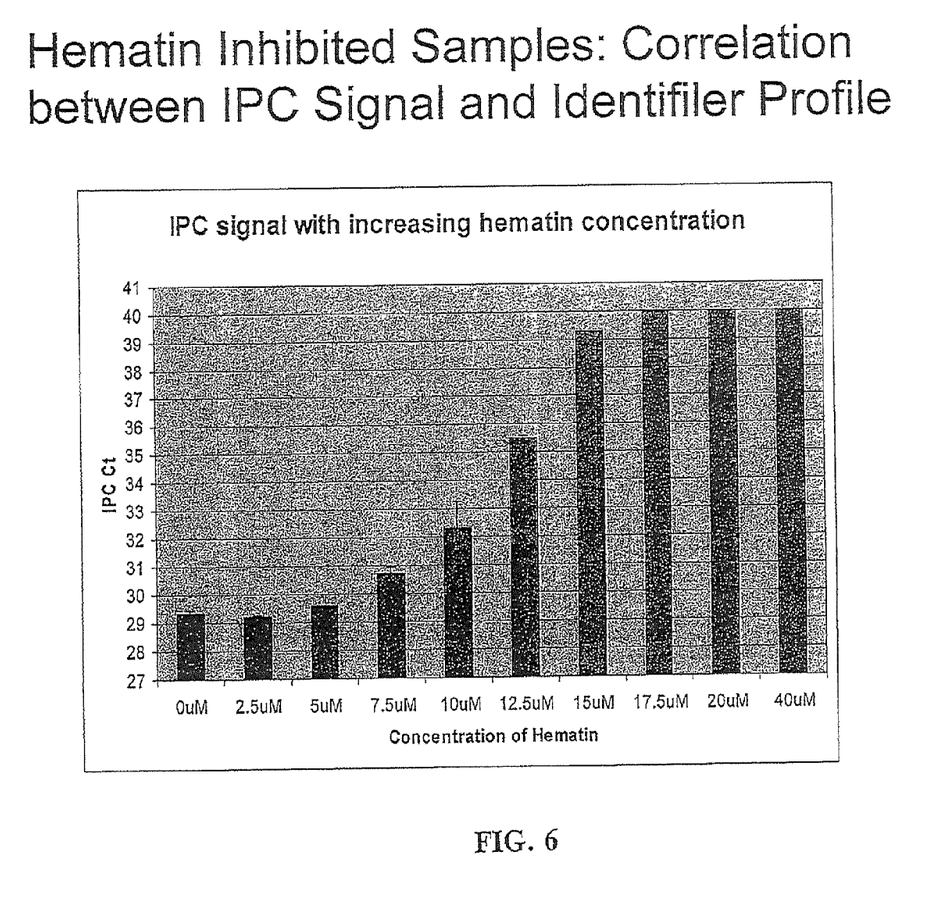
FIG. 6 is a bar graph indicating increasing IPC Ct value (decrease in IPC amplification signal) with increasing hematin concentration for inhibited samples

Incorporating the novel IPC template construct (SEQ ID NO: 1) on a suitable plasmid pCR®4-TOPO® into the multiplex real time PCR reaction, greatly enhanced the ability to detect the presence of PCR inhibitors. Other similar plasmids or vectors such as pUC 19, or pBR322 (available from Fermentas Life Sciences, Hanover, Md.) would also be useful for constructing a plasmid IPC containing SEQ ID NO:1 or SEQ ID NO:2. Such PCR inhibitors are typically agents that inhibit the activity of the thermostable polymerase in the PCR reaction. Such inhibitors include such diverse agents as polyphenols and phenolic compositions, tissue components, hematin, humic acid, indigo (a denim dye), carmine, bark extract, and soil extract. Reference to novel IPC template or IPC refers to a plasmid containing SEQ ID NO: 1. The positive cycle threshold value (Ct value) for the novel IPC shifts with increasing amount of PCR inhibitor (See FIGS. 5-6). The IPC Ct change also correlates well with Ct changes of human nuclear DNA targets (RPPH1, SEQ ID NO: 3) and human male (SRY, SEQ ID NO: 4) targets and of STR profiles. Methods utilizing SEQ ID NO: 1 as the IPC template are predictive of PCR inhibition by virtue of detecting the presence of very small amounts of PCR inhibitors, such as hematin and humic acid, as well as other similar inhibitors.

The quantity of total human nuclear DNA and human male DNA in a sample is derived by monitoring the amplification of RPPH1 target (SEQ ID NO: 3) and the SRY target (SEQ ID NO: 4), respectively. Typically, a control male DNA (such as Raji DNA or human male DNA from blood) is used for the generation of standard curves for both assays. Monitoring the simultaneously directed amplification of the novel IPC provides information about the presence and quantity of PCR inhibitors in the sample. The sizes of the PCR amplicons generated in the present assays, 140 nucleotide bases for the RPPH1 (SEQ ID NO: 3) and 130 nucleotide bases for the SRY (SEQ ID NO: 4), were optimized for obtaining STR profile for majority of the loci in STR multiplex kits such as Identifiler® (100-400 base pairs (bp)), Profiler Plus® (100-400 bp), COfiler® (100-350 bp), Yfiler® (100-400 bp), and MiniFiler™ (80-250 bp) (all kits available from Applied Biosystems, Foster City, Calif.), even with degraded samples.

The amplicons produced in the assay are detected by the binding of a labeled probe directed to the amplicon. For the RPPH1 (SEQ ID NO: 3) amplicon, the probe is SEQ ID NO: 9. For the SRY (SEQ ID NO: 4) amplicon, the probe is SEQ ID NO: 10. For the novel IPC sequence, the probe is SEQ ID NO: 13. The signal obtained from the label released from the bound probe with the amplicon determines the quantity of total human nuclear and human male DNA in a sample.

Figure 4:
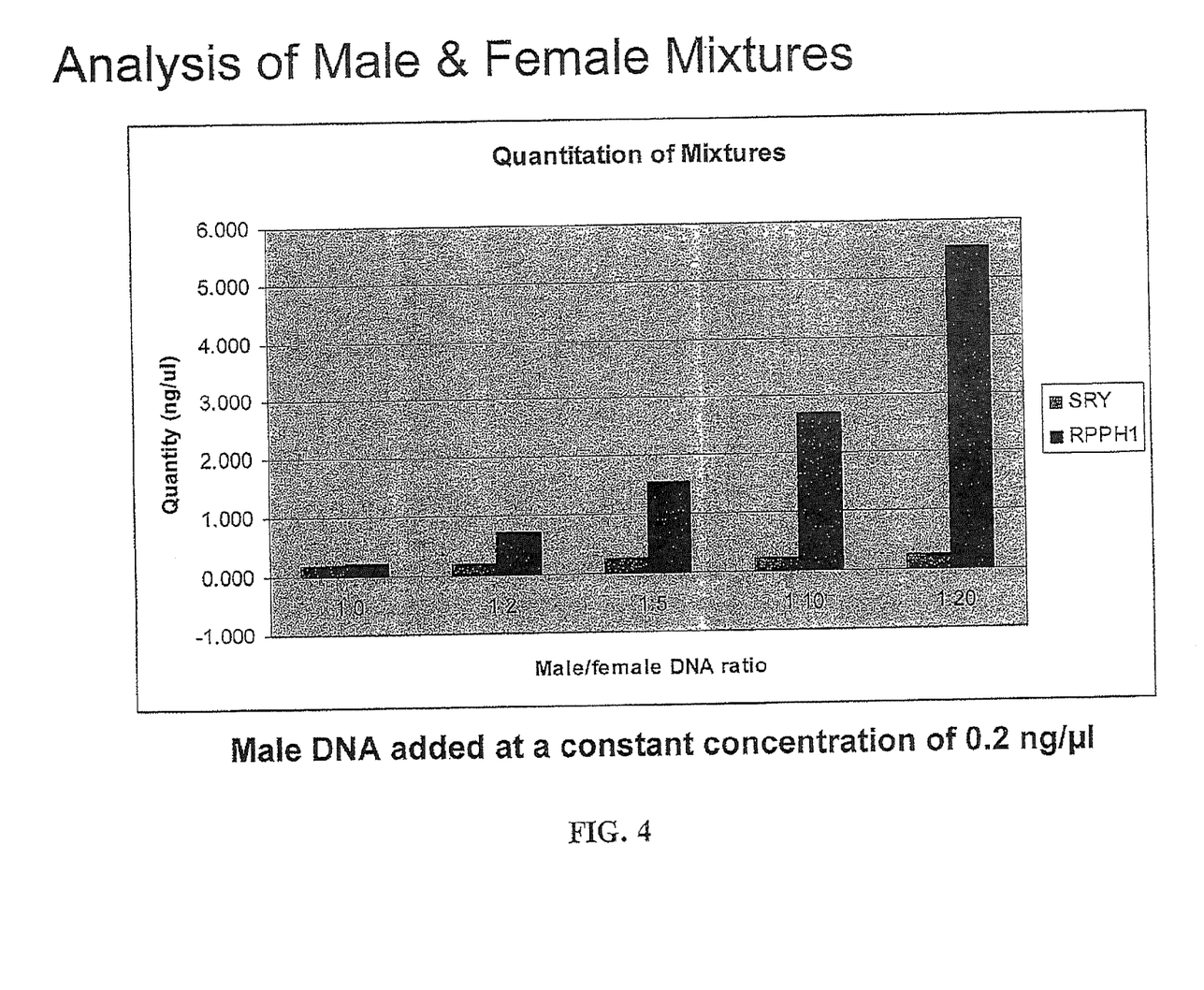
FIG. 4 is a bar graph showing the analysis of male and female DNA mixtures.

The multiplex assays utilizing detection of the RPPH1 (SEQ ID NO: 3) amplicon and SRY (SEQ ID NO: 4) amplicon as described herein exhibit human specificity with minimal cross-reactivity to DNA from other species (as shown in Example 3 and Table 2). The tested primer and probe concentrations were optimized to ensure that the Y-DNA was detected and quantified accurately in the presence of a large excess of female DNA (as described fully in Example 4 and FIG. 4). The ability of these multiplex assays to answer the foregoing three questions simultaneously is demonstrated using different biological samples such as blood, saliva, epithelial cells, and semen.

Optimization Incorporating Polyhydroxy Alcohols

Another aspect of the present methods relates to reducing the spectral bleed through (cross-talk) in non template control wells in multiplex Real-Time PCR assays, such as TaqMan® assays.

As described herein, Applicants have designed multiplex Real-Time PCR assays, for determining the mixture ratio of human nuclear and human male DNA and also to detect the presence of PCR inhibitors in a forensic biological sample prior to amplification for STRs. The assay is preferably performed on 7500 Real Time PCR System (Applied BioSystems, Foster City, Calif.), but is compatible with other suitable Real Time PCR Systems.

The present methods also relate to incorporating polyhydroxy alcohols, e.g. glycerol, for reducing the cross-talk by minimizing the probe-probe or probe-primer interactions and degradation of probes. Spectral overlap is a common observance in the multiplex real time PCR assays. Suitable fluorescent dyes (i.e. labels) for use in the 7500 system are FAM™ (6-carboxyfluorescein), VIC®, NED™ (yellow), TAMRA™ (tetramethylrhodamine) and ROX™ (6-carboxy-X-rhodamine), all commercially available, (Applied Biosystems, Foster City, Calif.). Other suitable fluorophores can be used, as long as they are capable of producing detectable signals in the desired assay system. Spectral overlap can produce false positive results for the no template control (NTC) utilized in the PCR assay. When this occurs, the assay must be repeated or requires a manual review of the data. Thus, false positive results in NTC due to spectral overlap result in lost time and wasted sample, which are undesirable in regulated laboratories such as a forensic DNA laboratory. Obtaining a positive cycle threshold value (Ct) for the NTC typically occurs due to one or more of the following conditions: poor spectral calibration, non optimal concentration of ROX (passive reference dye), non optimal concentration of primers and probes, or undesirable probe-probe or probe-primer interactions, degradation of probe etc. It is often difficult to identify a reason for the observed cross-talk in a multiplex real time PCR assay.

Incorporation of polyhydroxy alcohols such as glycerol in multiplex TaqMan® Real-time PCR assays provides the following advantages:

1. Reduction of the cross-talk in the NTC wells resulting from the degradation of probe or primer-probe and probe-probe interactions; and 2. Decrease in the variability in the Ct values and amplification curves.

Applicants have found that using polyhydroxy alcohols such as glycerol, improves the performance of multiplex real-time PCR assays. Amounts of glycerol used in the present methods include those within the ranges of 3%-5% of the reaction mix. The variation in the cross-talk between the FAM and VIC channels was significantly lower compared to the cross-talk in the absence of glycerol. While not wishing to be bound by theory, it is believed that the reduction in cross-talk is due to the stabilization of the probe or primer-probe, or the probe-probe interactions by addition of glycerol. In particular embodiments utilizing 5% glycerol, cross-talk was diminished, reducing the dRN in the VIC channel to 0.132 and the FAM channel to 0.122. In this manner, reducing the dRN in the VIC and or FAM channel avoids obtaining positive results from the NTC. Utilizing polyhydroxy alcohols improves assay results in multiplex Real-time PCR assays, such as the present assay and more generally in other Multiplex Real-time PCR assays, including TaqMan® assays.

Aspects of the present teachings may be further understood in light of the following examples, which should not be construed as limiting the scope of the present teachings in any way.

EXAMPLE 1

Triplex Multiplex Assays

The present triplex assays comprise co-amplification of the sex determining region Y or SRY (GeneID 6736) (SEQ ID NO: 4) on Y chromosome for quantification of human male DNA, the ribonuclease P RNA component H1 or RPPH1 (GeneID 85495) (SEQ ID NO: 3) on chromosome 14 for quantification of total human nuclear DNA, and a synthetic nucleotide template sequence (SEQ ID NO: 1) as an internal positive control (IPC). The TaqMan® probes for the measurement of human male DNA (SEQ ID NO: 10), was labeled with FAM™ (Applied Biosystems, Foster City, Calif.). The human nuclear DNA (SEQ ID NO: 9) was labeled with VIC® (Applied Biosystems, Foster City, Calif.). The novel IPC probe (SEQ ID NO: 13) was labeled with NED™ dye (Applied Biosystems, Foster City, Calif.). Information describing the commercial availability and instructions relating to TaqMan® assays and probes are provided by the manufacturer Applied Biosystems, Foster City, Calif. While the present assays are described as TaqMan® assays utilizing TaqMan® probes, other suitable fluorophores can be used, as long as they are capable of producing detectable signals in the desired assay system. Typically, multiplex probes are linear oligonucleotides ("oligo" ranging from 20-30 nucleotides) containing two labels, one at each end: a fluorophore reporter molecule (traditionally on the 5' end), and a quenching dye (traditionally on the 3' end). The probe can be tailored to desired specifications (i.e., type of fluorophore, type of quencher, locations of fluorophore and quencher, length of oligo). When excited by light, the fluorophore transfers energy to the quencher instead of fluorescing. During PCR, the polymerase cleaves the probe (liberates the probe) that has bound to the target template or amplicon sequence, separating the fluorophore and quencher to the extent that fluorescence resonance energy transfer (FRET) cannot occur. The result is that when light subsequently excites the liberated fluorophore (from the probe), fluorescence is produced.

The presently described multiplex assay was optimized in silico to avoid interactions between the oligonucleotides and minimize formation of primer-dimers. Pooled human male genomic DNA (EMD Biosciences. Inc. San Diego, Calif.), at a concentration of 200 ng/µl was used for the generation of standard curves for both assays. However, suitable human male genomic DNA could be obtained from other sources such as Raji cells (Raji DNA). The primer and probe concentrations were optimized to ensure that the human male DNA was detected and quantified accurately in the presence of a large excess of female DNA.

The DNA from anonymous donor samples (blood or buccal swabs) was extracted using standard procedures. The quantity of human DNA was determined by Quantifiler® human DNA quantification kit (Applied Biosystems, Foster City, Calif.). Multiplex Real-Time PCR Amplification reactions contained the following components.

10.5 µl of 2.5× Primer-Probe Mix, 12.5 µl of 2.0× Master Mix, and 2.0 µl of DNA sample. The 2.5× Primer-Probe Mix contained 1.75 µM of forward and reverse primers for SRY (SEQ ID NO: 7 and SEQ ID NO: 8) and RPPH1 (SEQ ID NO: 5 and SEQ ID NO: 6), 0.625 µM of TaqMan® probes for SRY (SEQ ID NO: 10) and RPPH1 (SEQ ID NO: 9) amplicons, 0.375 µM of forward and reverse primers for IPC template (SEQ ID NO: 11 and SEQ ID NO: 12), 0.425 µM of TaqMan® probe for IPC amplicon (SEQ ID NO: 13) and 5000 copies of IPC template in 10 mM Tris-HCl, pH 8.0 containing 0.1 mM EDTA. The primers were selected and designed based on the published sequences to obtain 140 and 130 bp fragments for RPPH1 and SRY targets, as described above. The IPC template was 130 bp synthetic polynucleotide (SEQ ID NO: 1) cloned into pCR®4-TOPO® plasmid (Invitrogen, Carlsbad, Calif.) by well-known techniques, the resulting plasmid shown in FIG. 7. Other suitable plasmids or vectors for use with the novel IPC templates SEQ ID NO: 1 or SEQ ID NO: 2 include, e.g. pUC19 or pBR322 (Fermentas Life Sciences, Hanover, Md.). The 2.0× Master Mix contained Reference dye (70 nM), dNTPs (0.4 mM), dUTP (0.8 mM), KCl (100 mM), 8.0 mM MgCl2, AmpliTaq® Gold DNA polymerase (0.5 U/µl) and standard preservatives in 100 mM Tris-HCl, pH 8.0.

Figure 2:
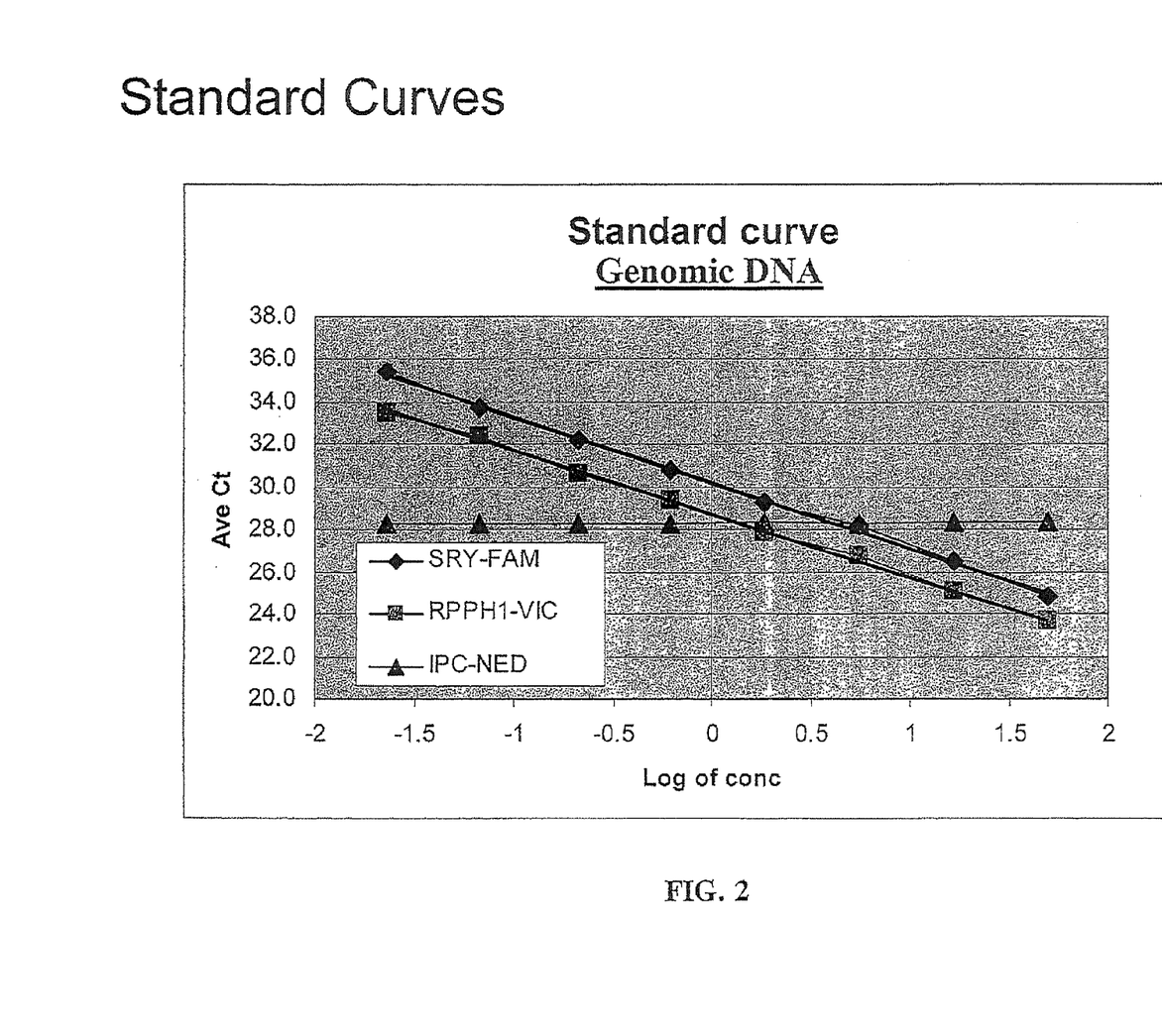
FIG. 2 is a standard curve of control male DNA.

Amplification reactions were performed in a 7500 Real-time PCR System (Applied Biosystems) following the manufacturer's instructions with conditions as follows: 50° C., 2 min; 95° C., 10 min; 40 cycles of 95° C., 15 sec and 60° C., 1.0 min. A standard curve (shown in FIG. 2) was constructed by using serial dilutions of human male genomic DNA (EMD Biosciences Inc., San Diego, Calif.) ranging from 23 pg/µl to 50 ng/µl. The data were analyzed using 7500 System SDS Software v1.2.3 (Applied Biosystems), the threshold value was 0.2.

EXAMPLE 2

Linearity and Quantification Range

The linearity and limits of quantification of the triplex assays, as described in Example 1, were determined by quantification of human DNA samples with quantities of DNA ranging from 23 pg/µl to 50.0 ng/µl in duplicate. As expected, the Ct value increased progressively with decrease in the amount of human DNA. A linear relationship between the Ct values and quantity of DNA template investigated was observed for both human nuclear and human male DNA. Ct values for the novel 130 bp IPC increased by about 0.5-1.0 at higher concentrations of human nuclear DNA because of the PCR competition. In general, the Ct values for the SRY target (SEQ ID NO: 4) were higher by 1 compared to the RPPH1 target (SEQ ID NO: 3). This observation correlates to the single copy of the Y chromosome target compared to two copies of autosomal target. The results indicate that the present triplex assay exhibits a high dynamic range and the lower limit of quantification determined at 23 pg/µl.

Figure 3:
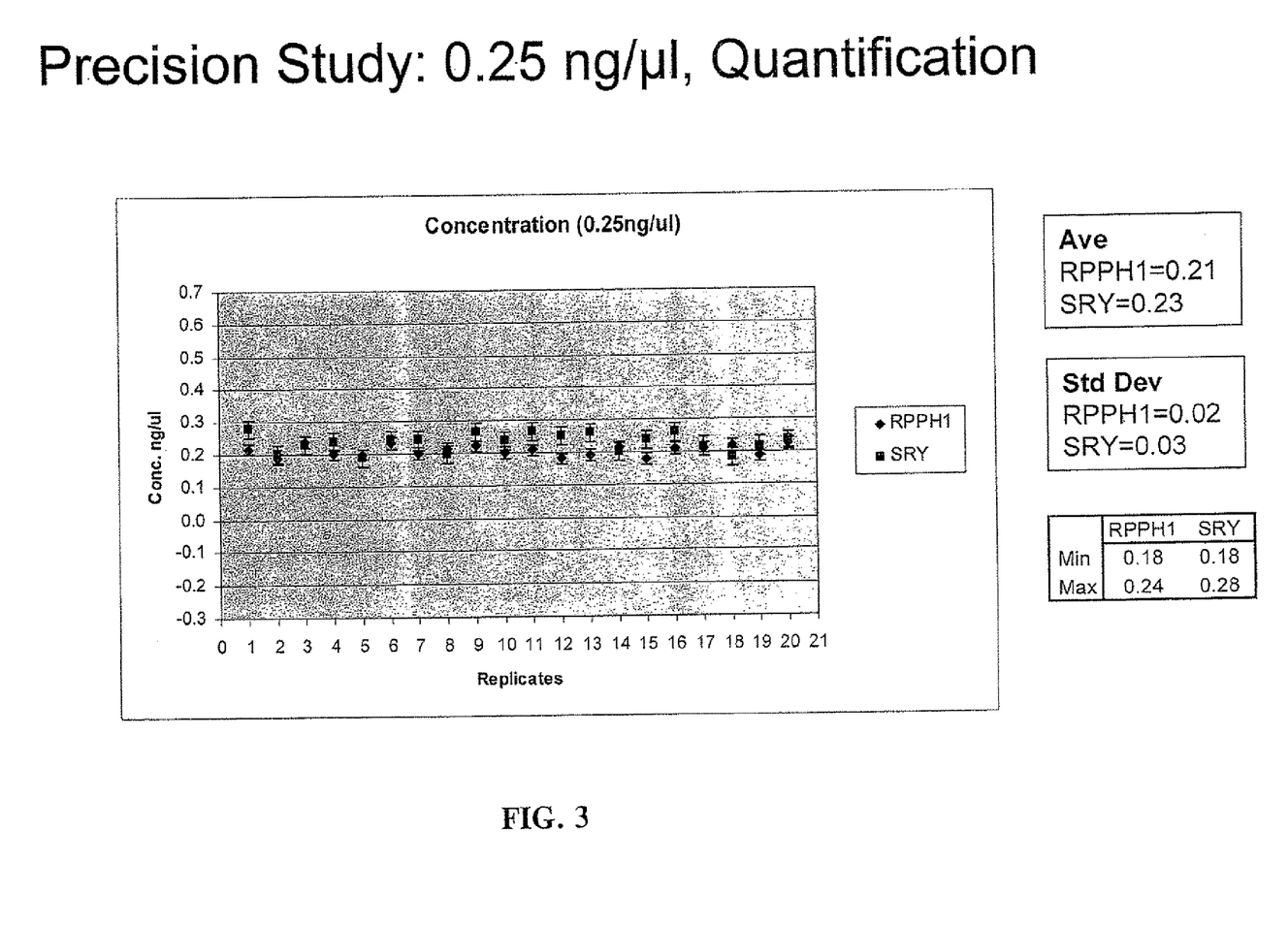
FIG. 3 is a graph showing quantification precision results at 0.25 ng/µl of DNA for RPPH1 and SRY amplicons.

Correlation studies were conducted using the Quantifiler® kit and the multiplex assay with Raji DNA at concentrations of 0.25 ng/µl, 1.0 ng/µl, and at 2.0 ng/µl. These results correlate well with Quantifiler® kits as shown below in Table 1. An exemplary graph showing precision results for 0.25 ng/µl for 20 replicates using the present assay is shown in FIG. 3.

TABLE 1

| Sample (ng/µl) | Multiplex SRY (SEQ ID NO: 4) | Multiplex RPPH1 (SEQ ID NO: 3) | Quantifiler ® Male | Quantifiler ® Human |
|---|---|---|---|---|
| 0.25 | 0.23 | 0.20 | 0.36 | 0.30 |
| 1.0 | 0.87 | 0.83 | 1.46 | 1.35 |
| 2.0 | 1.76 | 1.73 | 3.09 | 2.9 |

EXAMPLE 3

Species Specificity

The species specificity of the triplex assay was examined by amplification of 10.0 ng of DNA from orangutan, chimp, gorilla, macaque, dog, cow, pig, cat, chicken, fish (salmon), rabbit, mouse, rat, hamster, *Escherichia coli*, *Pseudomonas* sp., *Neisseria gonorrhoeae*, *Staphyloccus* sp. and *Saccharomyces* sp. None of the species investigated exhibited amplified products except for gorilla and chimp. Gorilla and chimp DNA exhibited VIC and FAM signal with Ct values of 37.9 (for RPPH1 (SEQ ID NO: 3) VIC labeled) and 30.7 (with SRY (SEQ ID NO: 4) FAM labeled), respectively, compared to a human specific signal of 26 Ct (for RPPH1 (SEQ ID NO: 3) VIC labeled) and 28.8 Ct (with SRY (SEQ ID NO: 4) FAM labeled). Thus, the primers and probes in the multiplex assay are specific for human DNA with some reaction with higher primate DNA, as shown in TABLE 2. The low level of gorilla and chimp signals will not interfere with distinguishing human samples from non primate animal samples, in routine forensic testing.

TABLE 2

| Species | RPPH1 Ave. Ct | SRY Ave. Ct |
|---|---|---|
| Orangutan | 40.0 | 40.0 |
| Chimp | 40.0 | 30.7 |
| Gorilla | 37.9 | 40.0 |
| Macaque | 40.0 | 40.0 |
| Dog | 40.0 | 40.0 |
| Cow | 40.0 | 40.0 |
| Pig | 40.0 | 40.0 |
| Cat | 40.0 | 40.0 |
| Chicken | 40.0 | 40.0 |
| Fish (Salmon) | 40.0 | 40.0 |
| Rabbit | 40.0 | 40.0 |
| Mouse | 40.0 | 40.0 |
| Rat | 40.0 | 40.0 |
| Hamster | 40.0 | 40.0 |
| Male (Raji) | 26.5 | 28.8 |
| Female (NA 14672a) | 26.2 | 40.0 |
| E. coli | 40.0 | 40.0 |
| Pseudomonas | 40.0 | 40.0 |
| Neisseria | 40.0 | 40.0 |
| Staphylococcus | 40.0 | 40.0 |
| Saccharomyces | 40.0 | 40.0 |

EXAMPLE 4

Male-Female Ratios

Male-female mixture samples were prepared by combining human male DNA with two human female DNA preparations. Purified genomic DNA from the Raji (male) and female (9947A) cell lines were combined according to various ratios (for example 1:0, 1:2, 1:5, 1:10, 1:20, 1:100, 1:500, 1:1000) to mimic sexual assault evidence samples. The mixtures were tested using the multiplex assay as described above to determine the concentration of total human nuclear DNA and male DNA. For example, the present multiplex assay can measure 50 pg of male DNA in the presence of up to 50 ng of female DNA (1:1000 ratio). Exemplary quantification results for male/female mixture samples are summarized in FIG. 4 and below in Table 4. These results show the multiplex assay of the present teachings to be a sensitive and specific method for determining the mixture ratio of human male and female DNA in a sample.

TABLE 4

| Male/Female Ratio | Average SRY Quantity | Average RPPH1 Quantity | SRY/RPPH1 theoretical ratio | SRY/RPPH1 measured ratio |
| --- | --- | --- | --- | --- |
| 1:0 | 0.179 | 0.207 | 1:0 | 1:1.15 |
| 1:2 | 0.203 | 0.719 | 1:3 | 1:3.5 |
| 1:5 | 0.240 | 1.550 | 1:6 | 1:6.4 |
| 1:10 | 0.205 | 2.690 | 1:11 | 1:13 |
| 1:20 | 0.242 | 5.540 | 1:21 | 1:22.8 |
| 1:100 | 0.224 | 23.180 | 1:101 | 1:103 |
| 1:500 | 0.302 | 143.740 | 1:501 | 1:476 |
| 1:1000 | 0.309 | 313.220 | 1:1001 | 1:1013 |

EXAMPLE 5

Detection of PCR Inhibitors

The ability of the present triplex assay to detect the inhibitors of PCR was examined by quantification of samples containing hematin or humic acid, common inhibitors of PCR that are often present in the forensic samples. Triplex reactions were performed as described above in Example 1 with the addition of varying amounts of humic acid (no humic acid, or 1 ng/μl to 30 ng/μl humic acid) or hematin (no hematin or 2.5 μM to 40 μM hematin). The reactions contained 5000 copies of plasmid containing the novel IPC (SEQ ID NO: 1) the amplification of which by specific primers serves as an indicator for the presence of PCR inhibitors. The reaction mixture contains an amount of labeled probe for detecting the SEQ ID NO:1 amplicon. The Ct values for the test samples containing the IPC inserted in a plasmid increased with increasing concentration of humic acid or hematin (shown in FIG. 5 and FIG. 6, respectively). The Ct value of >40.0 for samples containing the plasmid IPC indicates complete inhibition. These reactions are a reflection of the binding of the labeled probe to the plasmid sequence, and the subsequence cleavage of the probe by polymerase (producing fluorescence). The fluoresence produced correlates inversely with the presence of PCR inhibitors. That is, large amounts of fluorescence indicates a large amount of released probe, which indicates binding of the probe to the amplified plasmid sequence, and the appreciable absence of PCR inhibitors. Low or background fluorescence indicates no binding of the probe, no cleavage of the probe, and no amplification of the plasmid target sequence, indicating the presence of PCR inhibitors. The present results also exhibited a good correlation between the level of inhibition with the STR profiles generated using Identifiler® genotyping system. The results from these assays provide an accurate prediction of samples that would fail subsequent STR analysis because of the presence of one or more PCR inhibitors.

EXAMPLE 6

Quantification of Degraded DNA

Artificially degraded DNA samples were generated by sonication and subsequent DNase I treatment of high molecular weight Raji genomic DNA. Increasing units of DNase I (2, 3, 4, 5 and 6 units) were used to generate a series of samples with increasing levels of degradation. The samples were tested with the multiplex assay, as described in Example 1 to determine the quantity of amplifiable DNA. Using the quantification results obtained from the multiplex assay using SRY (SEQ ID NO: 4) and RRPH1 (SEQ ID NO: 3) target amplicons, the volumes of DNA required for two separate sets of AmpF/STR® Identifiler® kit reactions (Applied Biosystems, Foster City, Calif.) were calculated such that 1.0 ng of DNA was added in STR amplification reaction. The PCR products were run on an ABI Prism 3100 Genetic Analyzer. Complete STR profiles were obtained for up to 4 U of DNase I treatment and complete profiles were generated for the 5 U and 6 U DNase I treated samples. These results are summarized and shown in Tables 5-6.

TABLE 5

| Sample Name Ave. Conc. | Vol (μl) RPPH1 | STR peaks detected to give 1 ng | (out of 28) |
| --- | --- | --- | --- |
| intact | 11.68 | 0.09 | 28/28 |
| 2U | 3.86 | 0.26 | 28/28 |
| 3U | 2.61 | 0.38 | 28/28 |
| 4U | 1.35 | 0.74 | 28/28 |
| 5U | 1.04 | 0.96 | 26/28 |
| 6U | 0.23 | 4.28 | 24/28 |

TABLE 6

| Sample Name Ave. Conc. | SRY | Vol (μl) to give 1 ng | STR peaks detected (out of 28) |
| --- | --- | --- | --- |
| intact | 11.73 | 0.09 | 28/28 |
| 2U | 3.87 | 0.26 | 28/28 |
| 3U | 2.51 | 0.40 | 28/28 |
| 4U | 1.18 | 0.85 | 28/28 |
| 5U | 0.91 | 1.10 | 27/28 |
| 6U | 0.18 | 5.48 | 25/28 |

Kits

Various kits relating to multiplex assays will be useful. Such kits may comprise reagents for a polymerase chain reaction, along with primers for detecting RPPH1 and SRY targets, as well as the novel IPC template of SEQ ID NO: 1 or SEQ ID NO: 2 provided as an insert in a suitable plasmid such e.g. pCR® 4-TOPO® (Invitrogen, Carlsbad, Calif.), pUC19, or pBR322, and optionally other reagents for polymerase chain reaction and/or detection. A list of various components that may be included in a kit is shown in Table 7. Exemplary primer mix and PCR reaction mix compositions are shown in Tables 8-9. The assay results described herein utilized these typical primer and PCR reaction mixes, other suitable concentrations of reaction components can be utilized.

TABLE 7

Exemplary Multiplex Quantification Assay Kit (Assay)

| Reagent | Contents | Quantity | Storage |
|---|---|---|---|
| Primer Mix | Primer pairs for amplification of RPPH1, SRY and IPC. The TaqMan ® probes for RPPH1, SRY and IPC are labeled with VIC ®, FAM ® and NED ® dyes, respectively. In addition, this reagent contains IPC template. | 3 Tubes, 1.4 mL each | −15 to −25° C. (minimize freeze thaw cycles). |
| PCR Reaction Mix | MgCl₂, dNTPs, dUTP, bovine serum albumin, glycerol, passive reference dye and AmpliTaq Gold ® DNA Polymerase in buffer and salts. Sodium azide is incorporated as preservative. | 1 Tube, 5.0 mL | 2 to 8° C. |
| Quantification Standard | Human male genomic DNA (e.g. Raji DNA) | 1 Tube, 120 µL | −15 to −20° C. |
| Dilution Buffer | 10 mM Tris HCl buffer, pH 8.0 containing 0.1 mM EDTA | 2 Tubes, 2.0 mL each | 2 to 8° C. |

TABLE 8

Exemplary Primer Mix Components and Concentrations

| Component | Concentration at 2.5X |
|---|---|
| Fw RPPH1 primer (SEQ ID NO: 5)* | 1.5625 µM |
| Rev RPPH1 primer (SEQ ID NO: 6) | 1.5625 µM |
| probe RPPH1 (SEQ ID NO: 9) | 0.425 µM |
| Fw SRY primer (SEQ ID NO: 7) | 1.5625 µM |
| Rev SRY primer (SEQ ID NO: 8) | 1.5625 µM |
| probe SRY (SEQ ID NO: 10) | 0.425 µM |
| Fw IPC primer (SEQ ID NO: 11) | 0.375 µM |
| Rev IPC primer (SEQ ID NO: 12) | 0.375 µM |
| probe IPC primer (SEQ ID NO: 13) | 0.325 µM |
| Artificial template plasmid | 500 copies |
| TE (10 mM Tris HCl buffer, pH 8.0 containing 0.1 mM EDTA) | |

*Desalted primer and HPLC purified probes are used in these reactions.

TABLE 9

Exemplary PCR Reaction Mix

| Component | Concentration at 2.0X |
|---|---|
| 1M Tris-HCl pH 8.0 | 100 mM |
| 5 U/µl AmpliTaq Gold (or other suitable thermostable polymerase) | 0.5 U/µl |
| 25 mM each dNTP | 0.4 mM |
| 100 mM dUTP | 0.8 mM |
| 2M KCl | 100 mM |
| 1M MgCl₂ | 8 mM |
| 3 µM ROX Pass. Ref. | 70 nM |
| 20 mg/ml BSA (Roche) | 0.08 mg/ml |
| 10% NaN3 | 0.02% |
| 50% Glycerol (or other suitable polyhydroxy alcohol) | 16.00% |
| H₂O | varying amount |

The concentration of the components listed above in the PCR reaction mix can vary according to particular reaction conditions in amounts of e.g., +/−10%. Typical dilution buffer comprises 10 mM Tris HCl buffer at pH 8.0 with 0.1 mM EDTA.

The kits may further comprise any combination of PCR reaction mixtures, buffers, primers, thermostable polymerases, or suitable standards of predetermined amounts, including human male genomic DNA such as that from Raji cells (Raji DNA). These standards may be used to prepare a standard curve for a detection assay.

Typical kits will generally comprise one or more containers into which the biological agents are placed and, preferably, suitable aliquoted. The components of the kits may be packaged either in aqueous media or in lyophilized form.

The container means of the kits can generally include at least one vial, test tube, flask, bottle, or even syringe or other container means, into components may be placed, and preferably, suitably aliquoted.

The kits of the present invention can also typically include a means for containing the various reagent containers in close confinement for commercial sale. Such containers may include injection or blow-molded plastic containers into which the desired vials are retained.

Advantages of the Multiplex Assays

The present multiplex assays provide reliable information about a sample, typically a mixed forensic sample containing biological materials for interpretation in various downstream techniques, including for STR genotyping in forensic analysis. The results described herein illustrate the various advantages of the Multiplex assays in single, real-time PCR reactions using minimal evidence sample including:

Providing the quantity of human nuclear DNA in a sample to determine the quantity of extract for amplification of STR using multiplex kits.

Providing a correlation between the quantification value and STR profile. For samples tested in the present assays, an interpretable profile was obtained for the majority of the loci using STR genotyping systems such as Identifiler® (Applied Biosystems, Foster City, Calif.). For example, 13 out of the 15 amplified loci have fragment sizes larger than 140 bases. Likewise, 5 out of 8 amplified loci using MiniFiler™ (Applied Biosystems, Foster City, Calif.) have fragment size larger than 140 bases.

Providing the mixture ratio of human nuclear DNA and human male DNA for selection of STR genotyping systems. The results described using the Multiplex assays illustrate that samples that containing relatively small quantity of human male DNA compared to human nuclear DNA (heavy in female DNA) are preferably amplified for Y-STR loci using Yfiler® (Applied Biosystems, Foster City, Calif.).

Determining the presence of PCR inhibitors, facilitated by the amplification of IPC, allows for an informed choice of an STR kit that is designed for amplification of samples containing PCR inhibitors and/or degraded DNA. STR kits such as Identifiler® (Applied Biosystems, Foster City, Calif.) are designed for normal samples, while MiniFiler™ (Applied Biosystems, Foster City, Calif.) is designed for amplification of samples containing PCR inhibitors and degraded DNA. When samples exhibit complete inhibition, i.e., a failure to amplify the IPC, then re-purification of the extract can be performed prior to STR analysis.

All of the compositions and methods disclosed and claimed herein can be made and executed without undue experimentation in light of the present disclosure. While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

All literature and similar materials cited in this application, including but not limited to, patents, patent applications, articles, books, treatises, and internet web pages, regardless of the format of such literature and similar materials, are expressly incorporated by reference in their entirety for any purpose.

What is claimed is:

1. A kit comprising primer pairs and an internal plasmid control, wherein at least one primer pair is capable of specifically amplifying human Ribonuclease P RNA component H1 (RPPH1), at least one primer pair is capable of specifically amplifying human sex determining region Y (SRY) loci and at least one primer pair is capable of specifically amplifying SEQ ID NO:1 and wherein the internal plasmid control comprises SEQ ID NO:1.

2. The kit of claim 1, further comprising labeled probes for detecting the amplified human RPPH1 locus, the amplified human SRY locus, and amplified SEQ ID NO:1.

3. The kit of claim 2, wherein the RPPH1 probe is labeled with FAM; the SRY probe is labeled with VIC, and the SEQ ID NO:1 probe is labeled with NED.

4. The kit of claim 1, further comprising PCR reaction mix, a quantification standard, and a dilution buffer.

5. A kit comprising primer pairs and an internal plasmid control, wherein at least one primer pair is capable of specifically amplifying human RPPH1, at least one primer pair is capable of specifically amplifying human SRY loci and at least one primer pair is capable of specifically amplifying SEQ ID NO:2 and wherein the internal plasmid control comprises SEQ ID NO:2.

6. The kit of claim 5, further comprising a labeled probe for detecting the amplified human RPPH1 locus, the amplified human SRY locus, and SEQ ID NO:2.

7. The kit of claim 6 wherein the RPPH1 probe is labeled with FAM; the SRY probe is labeled with VIC, and the SEQ ID NO:2 probe is labeled with NED.

8. The kit of claim 5, further comprising PCR reaction mix, a quantification standard, and a dilution buffer.

* * * * *